US00PP19964P2

(12) United States Plant Patent
Rendle

(10) Patent No.: US PP19,964 P2
(45) Date of Patent: Apr. 28, 2009

(54) ***CORDYLINE* PLANT NAMED 'CORAL'**

(50) Latin Name: *Cordyline australis*
Varietal Denomination: Coral

(76) Inventor: Arthur Rendle, P.O. Box 113033, New Market, Auckland (NZ)

( * ) Notice: Subject to any disclaimer, the term of this patent is extended or adjusted under 35 U.S.C. 154(b) by 0 days.

(21) Appl. No.: 11/978,402

(22) Filed: Oct. 29, 2007

(51) Int. Cl.
*A01H 5/00* (2006.01)

(52) U.S. Cl. ..... Plt./383

(58) Field of Classification Search ..... Plt./383
See application file for complete search history.

*Primary Examiner*—Kent L Bell

(57) ABSTRACT

A new and distinct *Cordyline* cultivar named 'Coral' is disclosed, characterized by unique, variegated foliage of red, pink and purple, intensifying with age and higher light. Other characteristics are long, narrowly elliptic leaves, a strong root system and dense crown. 'Coral' also exhibits a tendency to remain vegetative and resist flowering.

1 Drawing Sheet

Figure 1:
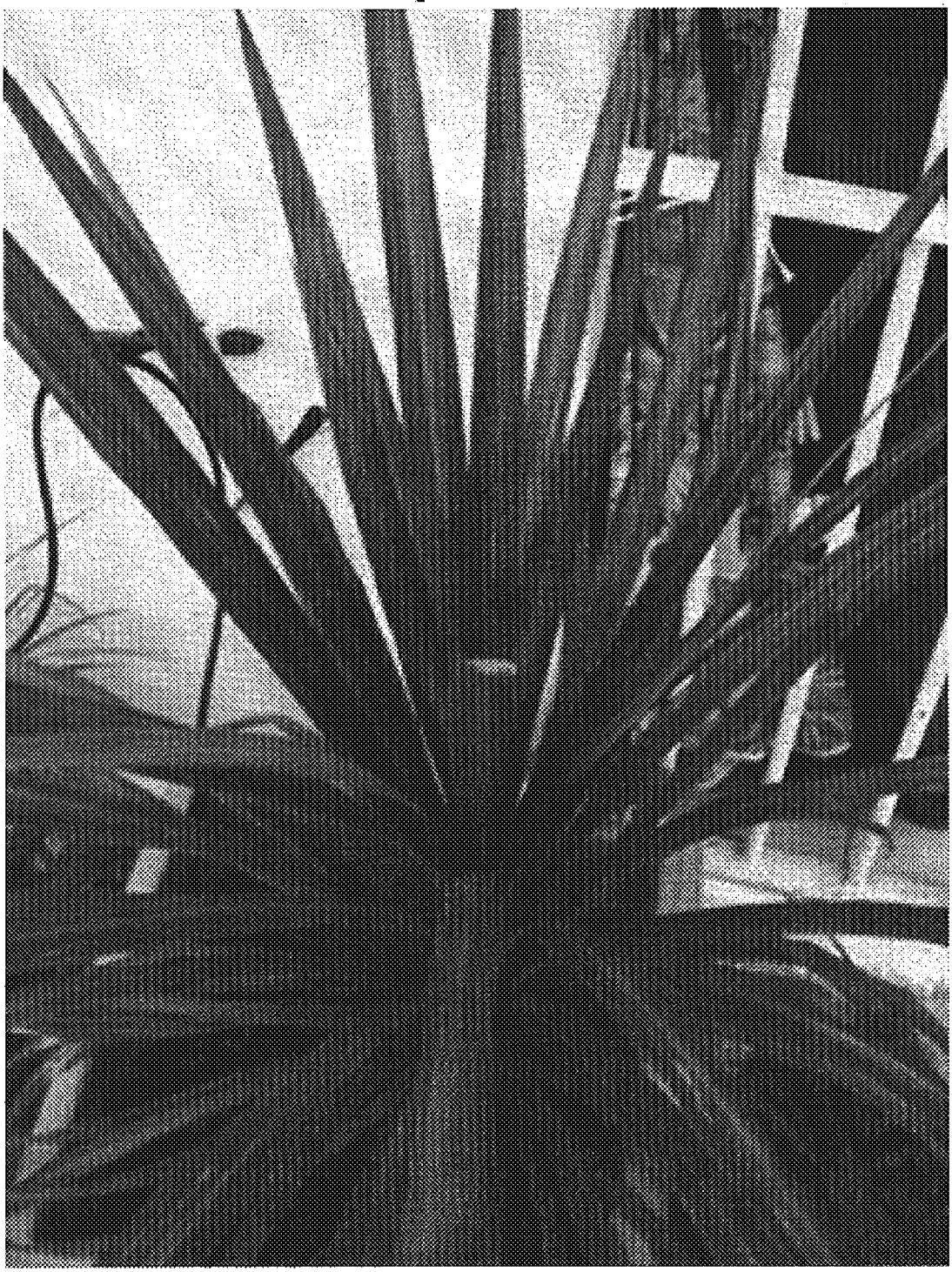

Latin name of the genus and species: *Cordyline australis*.
Variety denomination: 'CORAL'.

BACKGROUND OF THE INVENTION

The new cultivar is a product of a planned breeding program. The new variety originated from a cross pollination of the seed parent *Cordyline australis* 'Albertii,' an unpatented cultivar and the pollen parent *Cordyline australis* 'Purple Tower,' also unpatented, made by the inventor during December 1995.

It was discovered by the inventor, Arthur George Rendle, a citizen of New Zealand, in Spring of 1996 New Plymouth, New Zealand.

Asexual reproduction of the new cultivar 'Paradise' was first performed in Auckland, New Zealand, in a commercial greenhouse by vegetative root cuttings. Subsequently 'Paradise' has been reproduced by micro-propagation and has shown that the unique features of this cultivar are stable and reproduced true to type through 12 generations.

SUMMARY OF THE INVENTION

The cultivar 'Coral' has not been observed under all possible environmental conditions. The phenotype may vary somewhat with variations in environment such as temperature, and especially light intensity, without, however, any variance in genotype.

The following traits have been repeatedly observed and are determined to be the unique characteristics of 'Coral'. These characteristics in combination distinguish 'Coral' as a new and distinct *Cordyline* cultivar:

1. Unique variegated foliage of red, pink and purple, intensifying with age and higher light.
2. Long, narrowly elliptic leaves.
3. Strong root system.
4. Dense crown.
5. Tendency to remain vegetative and resist flowering.

Plants of the new cultivar 'Coral' are similar to plants of the seed parent; *Cordyline australis* 'Albertii', in most horticultural characteristics, however, plants of the new cultivar 'Coral' have red/purple/pink foliage while the seed parent 'Albertii' has green and yellow variegated foliage.

Plants of the new cultivar 'Coral' are similar to plants of the pollen parent; *Cordyline australis* 'Purple Tower', in most horticultural characteristics, however, plants of the new cultivar 'Coral' have stronger foliage variegation and a lighter overall foliage color. Additionally, the new variety as wider leaves.

The most similar commercial *Cordyline australis* varieties available to compare to 'Coral' are the parent varieties.

BRIEF DESCRIPTION OF THE PHOTOGRAPH

The accompanying photograph in FIG. 1 illustrates in full color a typical plant of 'Coral' grown in a greenhouse. The age of the plant is 1 year. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Coral' plants grown outdoors in grown in a greenhouse in Las Pallas, Murcia, Spain during the Winter of 2006 through Spring of 2007. Temperatures ranged from 5° C. to 12° C. at night to 5° C. to 20° C. during the day. Measurements and numerical values represent averages of typical plant types.

Botanical classification: *Cordyline australis* cultivar 'Coral.'

PROPAGATION

Time to rooting: 10 to 14 days at approximately 15° C. soil temperature, 22° C. air temperature.
Root description: Fine, fibrous.

PLANT

Growth habit: Upright perennial.
Height: Approximately 100 cm.
Blooming period: Not observed in commercial applications.
Plant Spread: Approximately 30 cm.
Growth Rate: Moderate
Branching Characteristics: Upright non-branching.

*Diameter of Stem.*—Approximately 2.5 cm.

*Stem length, measured as leafless section.*—Approximately 10 cm on a 1 year old plant. As the plant ages, lower leaves fall off, exposing a longer section of stem.

*Color of stem.*—Near RHS: Greyed-Orange 166B.

*Age of plant described.*—Approximately 1 year.

FOLIAGE

Leaf:

*Arrangement.*—Whorled.

*Average length.*—Approximately 70 cm.

*Average width.*—Approximately 1.5 cm at narrowest, approximately 3 cm at widest.

*Shape of blade.*—Very narrowly elliptic.

*Apex.*—Sharply Acute.

*Margin.*—Entire.

*Texture of top surface.*—Glaborous.

*Texture of bottom surface.*—Glaborous.

*Leaf internode length.*—2 mm.

*Color.*—Mature foliage upper side. Near RHS Purple 77A, with margins and stripes near RHS Red 47A. Mature foliage under side: Near RHS Purple 77A, with margins and stripes near RHS Red 47A.

*Venation.*—Type: Linear Venation coloration: Not visible due to variegation in foliage.

Petiole: Not present

FLOWER

Flowering has not been observed, and is not commercially important in this cultivar.

OTHER CHARACTERISTICS

Disease/resistance: Neither resistance nor susceptibility to diseases or pests has been observed in this variety.

Drought tolerance and cold tolerance: Hardy to −5° C. Tolerates temperatures above 40° C. Excellent drought tolerance. In a garden setting, 'Coral' can tolerate a minimum of 3 to 4 weeks without water undamaged.

Fruit/Seed production: Not observed.

What is claimed is:

1. A new and distinct cultivar of *Cordyline* plant named 'Coral' as herein illustrated and described.

* * * * *